US00PP18138P3

(12) United States Plant Patent
NeSmith

(10) Patent No.: US PP18,138 P3
(45) Date of Patent: Oct. 23, 2007

(54) SOUTHERN HIGHBUSH BLUEBERRY PLANT NAMED 'REBEL'

(50) Latin Name: ***Vaccinium* sp. Hybrid**
Varietal Denomination: Rebel

(75) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 1 day.

(21) Appl. No.: 11/297,654

(22) Filed: Dec. 7, 2005

(65) Prior Publication Data

US 2007/0130660 P1 Jun. 7, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Kent Bell
*Assistant Examiner*—June Hwu
(74) *Attorney, Agent, or Firm*—Greenlee Winner and Sullivan PC

(57) ABSTRACT

The most distinctive feature of the southern highbush blueberry, 'Rebel', is its combination of early fruit ripening, high yield, excellent fruit attributes especially size and scar, and its excellent plant vigor under field and high density growth conditions.

2 Drawing Sheets

Figure 1:
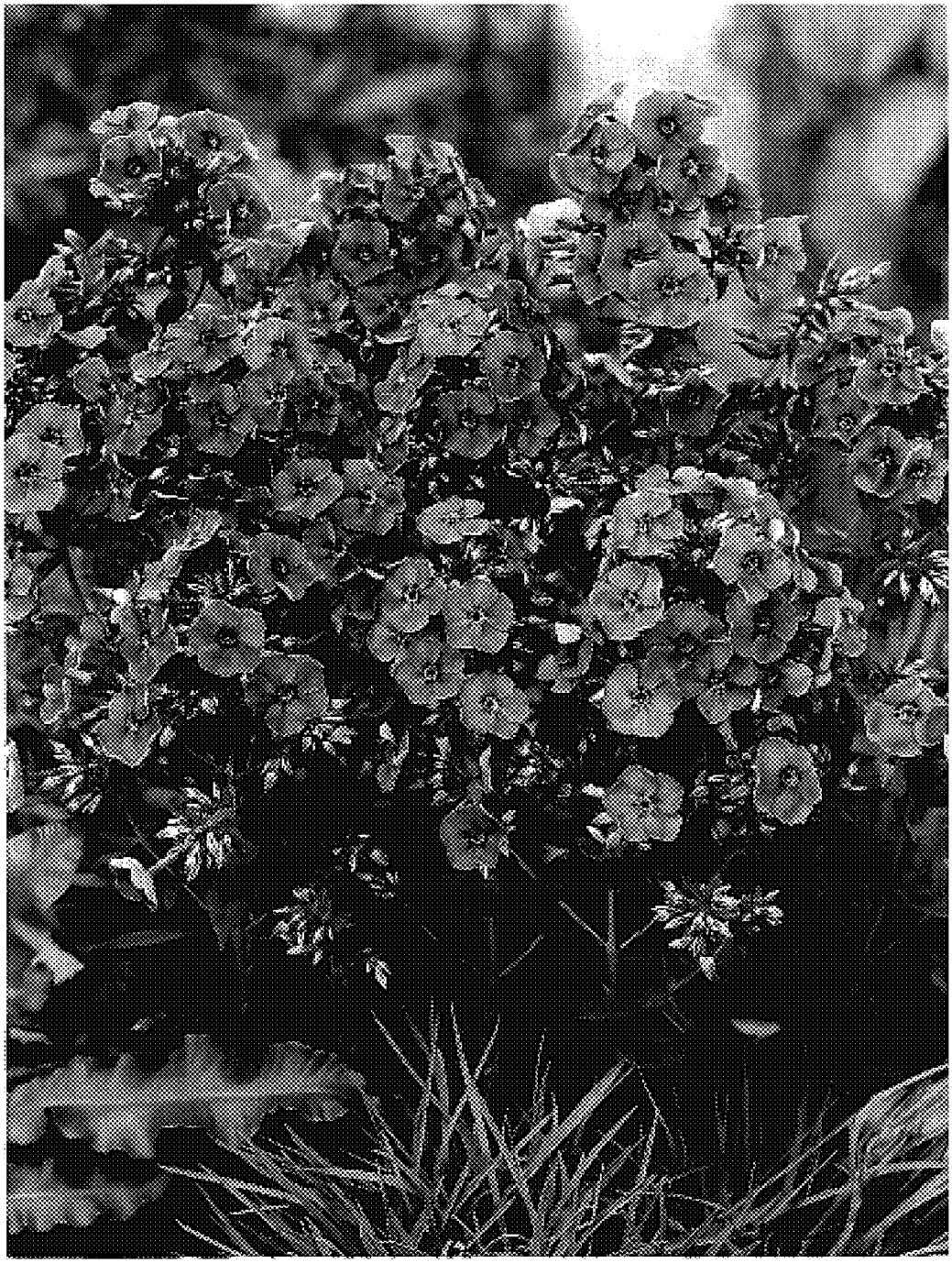

Botanical classification: *Vaccinium* sp. Hybrid.
Varietal denomination: 'Rebel'.

ACKNOWLEDGMENT OF FEDERAL RESEARCH SUPPORT

The invention was made in part with Federal funds pursuant to the Hatch Act.

BACKGROUND OF THE INVENTION

'Rebel' was selected in 2000 in Griffin, Ga. from open pollinated seedlings of FL 92-84 planted in Griffin in 1997. 'Rebel' is a hybrid containing predominantly *V. corymbosum*. FL 92-84, named 'Primadonna' by the University of Florida has not been patented to date. 'Rebel' differs from its female parent 'Primadonna' by being less upright in plant stature, and more spreading instead. Also, 'Rebel' leaves emerge readily during and shortly after flowering, whereas, 'Primadonna' tends to flower before leafing, often resulting in too few leaves to support good berry growth. 'Rebel' flowers 5 days after 'Primadonna', and ripens at a similar time. Finally, 'Rebel' is self-fruitful to a degree, whereas, 'Primadonna' is described are not being very self-fruitful. 'Rebel' has been tested in plantings at Alapaha and Griffin, Ga., since 2001. The selection was planted at a grower test site in 2003 in Ware County, Ga. and was planted in a high density test at Alapaha, Ga. in 2003.

'Rebel' has been asexually propagated on many occasions since 2000 by softwood cuttings at Griffin Ga. It roots readily from softwood cuttings and in all cases the clones propagated from cuttings have maintained the vegetative and fruit characteristics of the original selection.

'Rebel' has been primarily compared with the current, early southern highbush standard, 'Star' (U.S. Plant Pat. No. 10,675), grown under field conditions at Alapaha and Griffin, Ga. over a 3 year period.

Over the 3 year period 2003–2005, the date of 50% flowering of 'Rebel' was an average of 3 days earlier than 'Star', although this was not significantly different at the 10% probability level. The average date of 50% fruit ripening of 'Rebel' was significantly earlier by 8 days than 'Star', which has been highly acclaimed for its earliness.

Over the same period, the average berry size (7.8 vs. 7.0), berry scar (8.3 vs. 7.8), berry color (8.1 vs. 7.6) and berry firmness (7.8 vs. 7.6) for 'Rebel' was better than 'Star'. All values are based on a 1 to 10 score, with 10 being the most desirable and a value of 6–7 generally considered to be the minimum acceptable rating for a commercial cultivar. The plant vigor rating of 'Rebel' at 7.8 was greater than that of 'Star' at 6.4.

The fruit yield in 2005 on plants established in 2001 at Griffin, Ga. began significantly earlier for 'Rebel', which had a yield of 600 g/plant compared to less than 100 g/plant for 'Star' on May 18$^{th}$, and the final yield of 1700 g/plant was also significantly greater than 'Star' at 900 g/plant.

Some growers in Georgia are growing southern highbush blueberries in a high density system utilizing pine bark beds. High density plantings were established during 2003 at Alapaha and Ware County, Ga., to evaluate the performance of 'Rebel' compared to 'Star' and 'O'Neal' (non patented) under these conditions. 'Rebel' showed earlier production of fruit (210 g/plant by May 11) than 'Star' and 'O'Neal' (less than 30 g/plant), and a higher final yield (450 g/plant) than 'Star' (220 g/plant) and 'O'Neal' (390 g/plant). Over a 2 year period, 2004 and 2005, under high density planting, 'Rebel' flowered 3 days earlier than 'Star' and 8 days earlier than 'O'Neal', and 50% ripening was 8 days earlier than 'Star' and 16 days earlier than 'O'Neal'. Under these growth conditions the berry characteristics, size, scar, color and firmness of 'Rebel' were similar or better than 'Star' and 'O'Neal', and the plant vigor, at a rating of 9.1 was significantly better than 'Star' (7.8) or 'O'Neal' (6.8).

SUMMARY OF THE INVENTION

'Rebel' is an early season southern highbush blueberry having highly favorable fruit attributes especially size and scar. It is precocious, high yielding and has excellent plant vigor. It has similar chill hour requirements to other early season Southern highbush varieties, in the range of 400 to 450 hours.

DESCRIPTION OF THE PHOTOGRAPHS

FIG. 1 shows a cluster of berries, Apr. 26, 2004.

Figure 2:
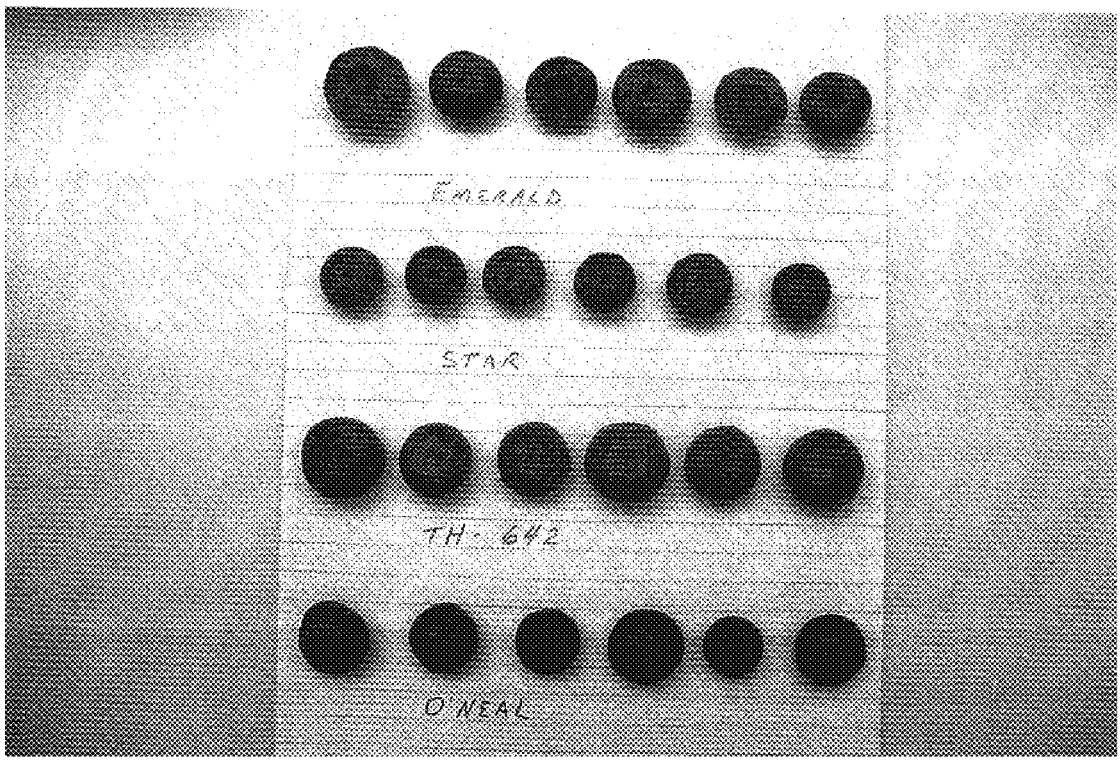

FIG. 2 shows fruit size of 'Rebel' (TH642) compared to 'Emerald' (U.S. Plant Pat. No. 12,165), 'Star' (U.S. Plant Pat. No. 10,675), and 'O'Neal'. May 11, 2005.

BOTANICAL DESCRIPTION OF THE PLANT

The following is a detailed description of the botanical and pomological characteristics of 'Rebel'. Where dimensions, sizes, colors, and other characteristics are given, it is to be understood that such characteristics are approximations and averages set forth as accurately as practicable. Color data are presented in Royal Horticultural Society Colour Chart designations. The descriptions reported herein are largely from specimen plants grown in Alapaha, Ga. and Griffin, Ga., with supplemental irrigation. Plants were 2 to 4 years old.

Plant:

*Size.*—Reaches 1.3 to 1.8 m tall by 4 years. Four-year-old 'Rebel' plants in southeast Georgia reach a height of 1.2 to 1.5 m at the center of the plant. Plant width at the base is 0.4 to 0.6 m, and width at the top of the bush is 1.0 to 1.2 m.

*Growth habit.*—Generally spreading, with numerous canes arising from the crown.

*Growth.*—Very high vigor. Grows moderately well in heavy Piedmont soils where most southern highbush varieties die out after 3 years.

*Productivity.*—Medium to high, averaging 3 to 4 lbs per plant each year for 2 to 3 year old plants grown in bark beds with irrigation.

*Cold hardiness.*—Similar to other southern highbush cultivars such as 'Star' and 'O'Neal'.

*Chilling requirement.*—Plants require 400 to 450 hours of temperatures at or below 45° F. (7° C.) to induce normal leafing and flowering during the spring.

*Leafing.*—Plants readily break numerous leaf buds simultaneously with anthesis.

*Canes.*—Canes 3 years old and older can be 15 to 20 mm in diameter; color is Grey Brown 199B. 2 year old wood is 6 to 8 mm in diameter; color is Yellow-Green 153D. Current season shoot is 2 to 3 mm in diameter; color is Yellow-Green 145A. Surface texture of 'Rebel' canes less than 3 years old are smooth. Canes 3 to 4 years old can become rough with some growth fissures and flaking bark. As canes become older, they eventually become nearly smooth once again.

*Diseases.*—More tolerant to septoria leaf spot then 'Star'.

Foliage:

*Leaf color.*—Healthy mature leaves: top side of leaf color is Green 137A, under side of leaf color is Yellow-Green 147C.

*Leaf arrangement.*—Alternate, simple.

*Leaf shape.*—Elliptic.

*Leaf margins.*—Nearly entire, slightly crenate near base.

*Leaf venation.*—Reticulate.

*Leaf apices.*—Acuminate.

*Leaf bases.*—Acute to acuminate.

*Leaf dimensions.*—Length 75 to 85 mm; width 35 to 45 mm.

*Leaf surface.*—Smooth, with moderate to heavy wax for a highbush cultivar.

*Petioles.*—Small, 3.0 to 4.5 mm long. Color is Yellow-Green 152D.

Flowers:

*Date of 50% anthesis.*—March 3 (3 year average in southeast Georgia). Blooming or flowering season for 'Rebel' begins around February 21$^{st}$ (10%) in southeast Georgia, reaching 50% bloom on March 3$^{rd}$ on average. Plants are 90% or more in bloom by March 13$^{th}$.

*Flower shape.*—Urceolate.

*Flower bud number.*—Medium to high.

*Flowers per cluster.*—5 to 8.

*Flower fragrance.*—Yes. 'Rebel' flowers have a slight rose to fruity fragrance if stored in an enclosed vial for 10 to 15 minutes after harvesting the blossoms.

*Corolla color.*—White 155D open flower.

*Corolla length.*—9.0 to 10.0 mm.

*Corolla width.*—5.9 to 6.6 mm.

*Corolla aperture width.*—2.5 to 3.0 mm.

*Flower penducle.*—Length 8 to 10 mm; Color Yellow-Green 145B.

*Flower pedicle.*—Length 3 to 4 mm; Color Green 145B.

*Calyx* (*with sepals*).—Diameter 5.0 to 5.5 mm; color Green 137B.

*Stamen.*—Length 6.5 to 7.0 mm; number per flower 10; filament color: Yellow-Green 145C.

*Style.*—Length 8.0 to 9.0 mm; color Yellow-Green 145A.

*Pistil.*—Length 11.0 to 12.0 mm; ovary color (exterior) Green 137D.

*Anther.*—Length 4.0 to 4.5 mm; number 10; color Greyed-Orange 167A.

*Pollen.*—Abundance: medium; color Yellow-Orange 14D.

The cultivar has a moderate degree of self-compatibility. It should be grown with another cultivar such as 'Star', 'O'Neal', or 'Palmetto' (U.S. Plant patent application Ser. No. 10/909,650, issued on Jul. 4, 2006 as U.S. Plant Pat. No. 16,756).

Fruit:

*Date of 50% maturity.*—May 3 (3 year average in southeast GA). In southeast Georgia, 'Rebel' on average has 10% ripe berries on April 22$^{nd}$, 50% on May 3$^{rd}$, and 90% ripe berries by May 15$^{th}$.

*Fruit development period.*—60 to 65 days.

*Berry color.*—With wax Violet-Blue 97C; with wax removed Greyed-Purple 187A to Black 202A.

*Berry surface wax abundance.*—High.

*Berry flesh color.*—Yellow-Green 145C to Green-White 157A.
*Berry weight.*—1st harvest 2.5 g to 3.0 g; $2^{nd}$ harvest 1.8 g to 2.2 g.
*Berry shape.*—'Rebel' berry shapes is nearly spherical.
*Fruit stem scar.*—Small, dry, no tearing.
*Berry firmness.*—Good.
*Berry flavor and texture.*—Mild flavor, excellent texture.
*Storage quality.*—Good to very good.
*Suitability for mechanical harvesting.*—Not likely.
*Uses.*—Primarily used as fresh fruit for shipping.

Seed:

*Seed abundance in fruit.*—Low to medium.
*Seed color.*—Greyed-Orange 165B.
*Seed dry weight.*—32.8 mg per 100 seed.
*Seed size.*—1.2 to 1.8 mm long for fully developed seeds.

I claim:

1. A new and distinct variety of southern highbush blueberry plant, substantially as illustrated and described.

* * * * *